United States Patent [19]
Lee et al.

[11] Patent Number: 5,342,288
[45] Date of Patent: Aug. 30, 1994

[54] TRACTION SPLINT

[76] Inventors: Roger Lee, 9533 Sunnyside Ave., Ben Lomond, Calif. 95005; Paul Martin, 38 Puffin Ct., Campbell, Calif. 95008

[21] Appl. No.: 924,193

[22] Filed: Aug. 3, 1992

[51] Int. Cl.⁵ .............................................. A61F 5/00
[52] U.S. Cl. ............................................. 602/5; 602/16; 602/23
[58] Field of Search ............ 602/5, 6, 9, 10, 12, 602/16, 23, 26, 27, 32, 33, 34, 35, 36, 38–40

[56] References Cited

U.S. PATENT DOCUMENTS

| | | | |
|---|---|---|---|
| 340,971 | 5/1886 | Aloe | 602/16 |
| 1,573,296 | 2/1926 | Brasell . | |
| 1,879,001 | 9/1932 | Allen | 602/23 |
| 2,198,908 | 4/1940 | Ellis | 128/84 |
| 2,252,607 | 8/1941 | Baker | 602/23 |
| 2,260,216 | 3/1941 | Doyle | 128/85 |
| 2,319,609 | 7/1941 | La Crosse | 128/84 |
| 2,384,779 | 2/1942 | Williams | 128/84 |
| 2,394,653 | 2/1946 | Auerhaan | 602/23 |
| 2,926,662 | 3/1960 | Pile | 602/16 |
| 3,419,002 | 12/1968 | Santosus | 602/23 |
| 3,906,942 | 9/1975 | Lumb, Jr. | 128/84 |
| 3,942,521 | 3/1976 | Klippel | 128/85 |
| 4,265,230 | 5/1981 | Jordon | 128/87 R |
| 4,911,152 | 3/1990 | Barnes et al. | 128/84 C |

*Primary Examiner*—Michael A. Brown
*Attorney, Agent, or Firm*—Jack M. Wiseman

[57] ABSTRACT

A traction splint for a long bone extremity fracture in which the length of the frame of the traction splint and the angle of the ischial pad of the traction splint relative to the frame are adjusted simultaneously. The ischial pad is pivotally connected to the frame and the pivotal movement of the ischial pad relative to the frame is restricted or limited up to 35°.

5 Claims, 8 Drawing Sheets

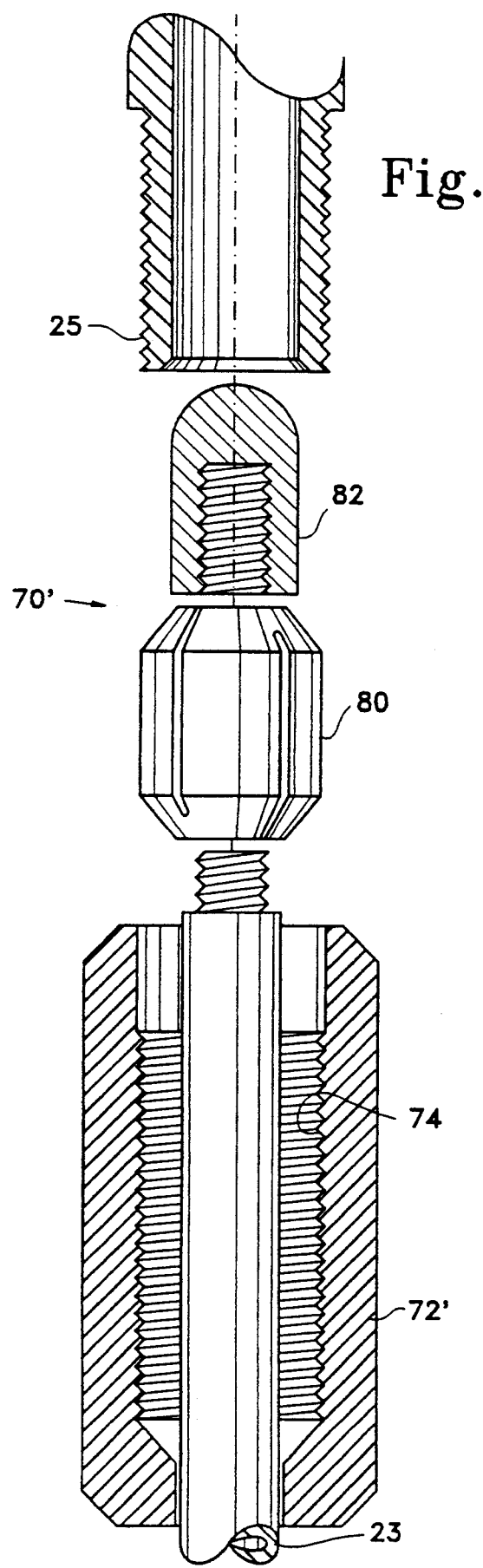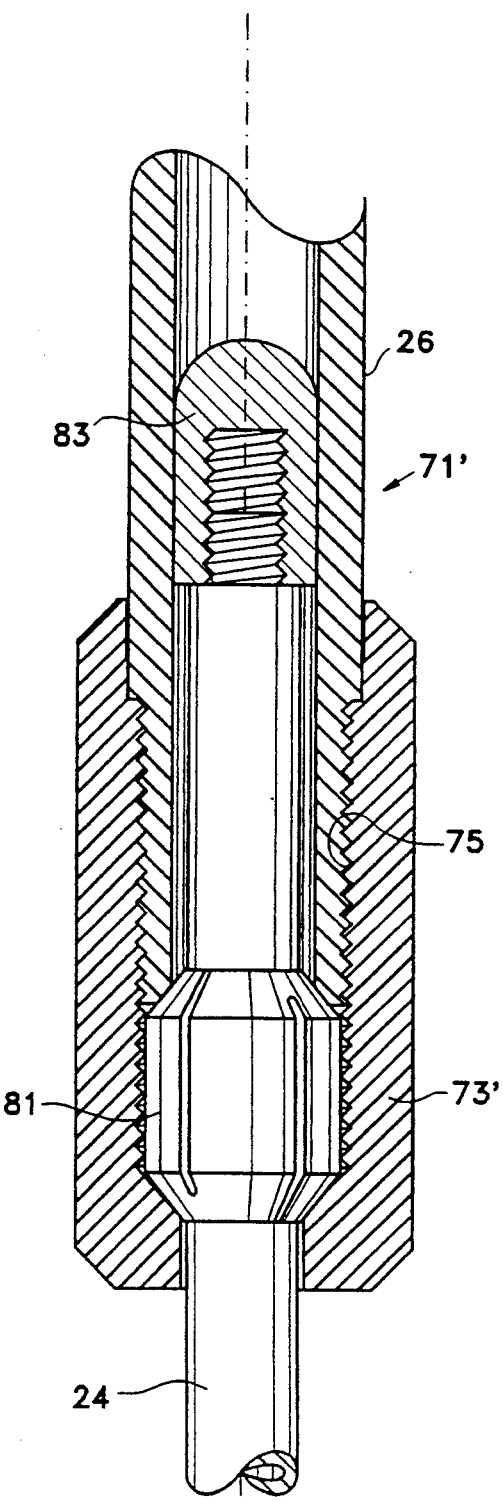

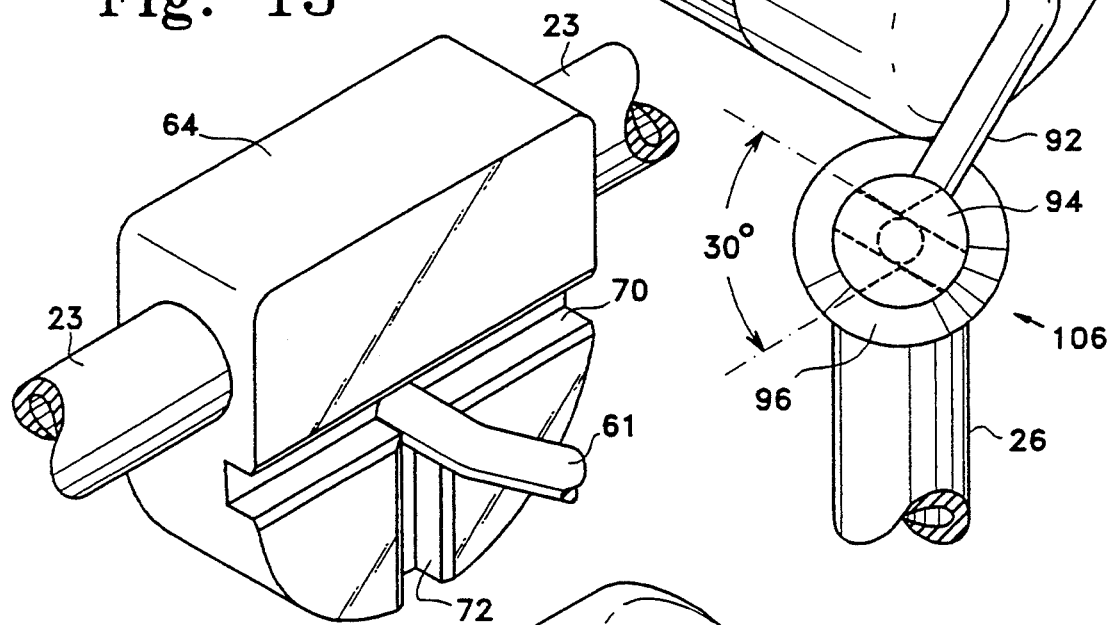
Fig. 11
Fig. 13
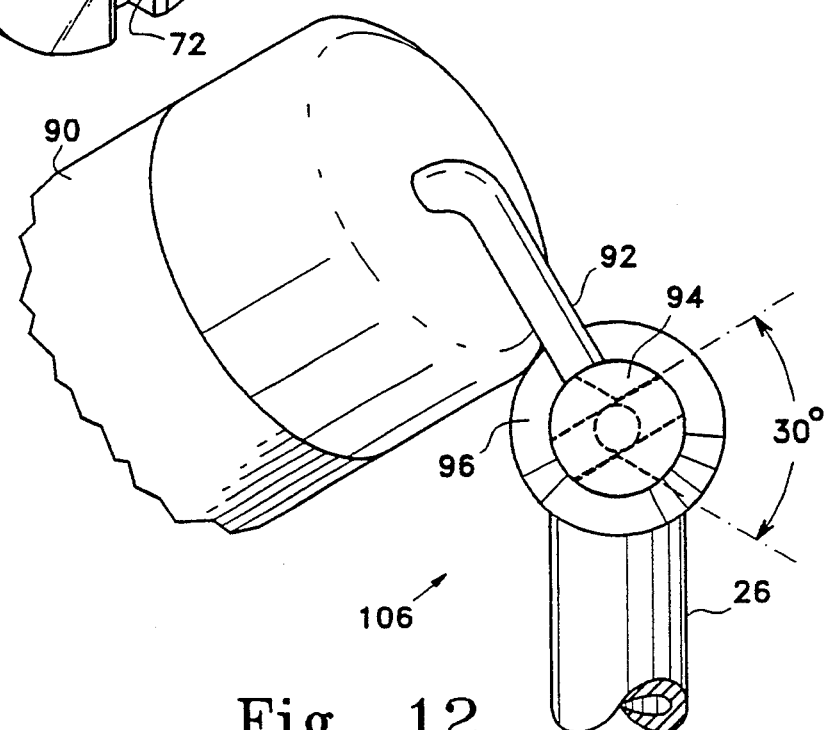
Fig. 12

TRACTION SPLINT

BACKGROUND OF THE INVENTION

The present invention relates in general to splints used for the temporary support of an injured limb, and more particularly to a splint used for the stabilization and traction of a long bone extremity fracture.

Heretofore, long bone traction splints employed ischial pads for fixed placement in the vicinity of proximal femoral bone. While a long bone traction splint has been made with the ischial pads having pivotal movement, such long bone traction splints were not arranged for simultaneous adjustment of the extent of a singular opposing side member of the frame and the angular adjustment of the ischial pad. Additionally, the angular movement of the ischial pad relative to the frame of the traction splint was not selectively restricted or limited.

In the U.S. Pat. No. 4,419,991, to Lee, issued on Dec. 13, 1983, for a Splint, there is disclosed a splint that includes upper and lower limb support sections. The support sections are connected so that one section of the frame can be adjusted to a position inclined upwardly or downwardly relative to the other section of the frame, or can be moved to a position extending laterally at an angle away from the other section of the frame, or can be adjusted to a position involving up, down and lateral movement of the sections of the frame for the purpose of angulated limb setting.

Reel Research And Development Inc. of Ben Lomond, Calif., has manufactured and sold a REEL SPLINT 8800 SERIES traction splint in which there are upper and lower limb support sections. The limb support sections are connected so that one section of the frame can be adjusted to a position inclined upwardly or downwardly relative to another section of the frame, or can be moved to a position extending laterally at an angle away from the other section of the frame, or can be adjusted to a position involving up, down and lateral movement of the sections of the frame. Additionally, the upper support section of the splint includes an ischial pad having pivotal movement. The REEL SPLINT 8800 Series traction splint also included devices for holding the parallel side members of the lower support section of the frame in the selected positions for adjusting the length of the lower section of the frame. At the end of the splint body opposite the ischial pad are swivel connectors for detachable traction mechanism and a retractable support stand in the vicinity of the foot of the frame.

Dyna Med, Inc. of Carlsbad, Calif., has manufactured and sold HARE traction splints, such as the classic HARE traction splint and the TRAC III traction splint in which the traction splint includes a linear and fixed ischial pad. Dyna Med has also manufactured and sold a HARE compact traction splint which includes a fixed perineal pad. Minto Research and Development of Redding, Calif., has manufactured and sold a SAGER 204 traction splint which is positioned between the patient's legs, resting the ischial perineal cushion against the pubis.

The U.S. Pat. No. 3,477,428, to Hare, issued on Nov. 11, 1969, for Combined Splint And Traction Device discloses an arcuate cradle swivelly mounted on tubular sections of a frame, the length of which can be adjusted. A U-shaped support member is attached to rods of the frame at the foot of the splint. An arrangement at the foot of the traction splint applies traction to the injured limb.

In the patent to Holmes, U.S. Pat. No. 4,328,794, issued on May 11, 1982, for Traction Splint, there is disclosed a retractable U-shaped support leg at the foot of a frame and a traction applying mechanism at the foot of the frame. A U-shaped section joins adjacent sides of the frame which is located on the opposite end of the frame with respect to the traction applying mechanism.

SUMMARY OF THE INVENTION

A traction splint in which a generally transversely disposed ischial pad is positioned adjacent parallel side members of a frame and the ischial pad has selectively limited pivotal movement relative to the side members of the frame.

A traction splint in which the length of at least one side member of parallel side members of a frame is adjustable simultaneously with the angular adjustment of an ischial pad relative to the side members of the frame, the angular adjustment of the ischial pad relative to the side members is selectively limited.

An object of the present invention is to provide a traction splint for adjusting simultaneously the length of at least one side member of parallel side members of a frame and the angle of an ischial pad relative to the side members of the frame, the angular adjustment of the ischial pad being selectively limited to facilitate the adjustment of the ischial pad for full engagement with the ischial tuberosity. Another object of the present invention is to provide a traction splint for adjusting simultaneously the length of at least one side member of parallel side members of a frame and the pivotal movement of the ischial pad relative to the side members of the frame, the pivotal movement of the ischial pad being selectively limited to facilitate the placement of the ischial pad to a desired location at the patient's posterior inguinal crease.

BRIEF DESCRIPTION OF THE DRAWINGS

FIG. 9 is an enlarged, fragmentary exploded axial sectional view, partially in elevation, taken along lines 9—9 of FIG. 1 to illustrate a releasable locking arrangement for adjustably securing telescopically received members of a parallel side member of the frame for adjusting the length of the side member.

FIG. 10 is an enlarged, fragmentary axial sectional view, partially in elevation, taken along lines 9—9 of FIG. 1 to illustrate a releasable locking arrangement for adjustably securing telescopically received members of a parallel side member of the frame of the traction splint shown in FIGS. 1-3 to set the length of the side member.

FIG. 11 is an enlarged, fragmentary perspective view of one end of the ischial pad pivotally connected to a parallel side member of the frame of the traction splint shown in FIGS. 1-3.

FIG. 12 is an enlarged, fragmentary perspective view of one end of the ischial pad pivotally connected to a parallel side member of the frame of the traction splint shown in FIGS. 1-3 illustrated at a different angular displacement than the angular displacement shown in FIG. 11.

FIG. 13 is an enlarged, fragmentary perspective view of a retractable stand located in the vicinity of the foot of the traction splint shown in FIGS. 1-3.

DESCRIPTION OF THE PREFERRED EMBODIMENT

Figure 1:
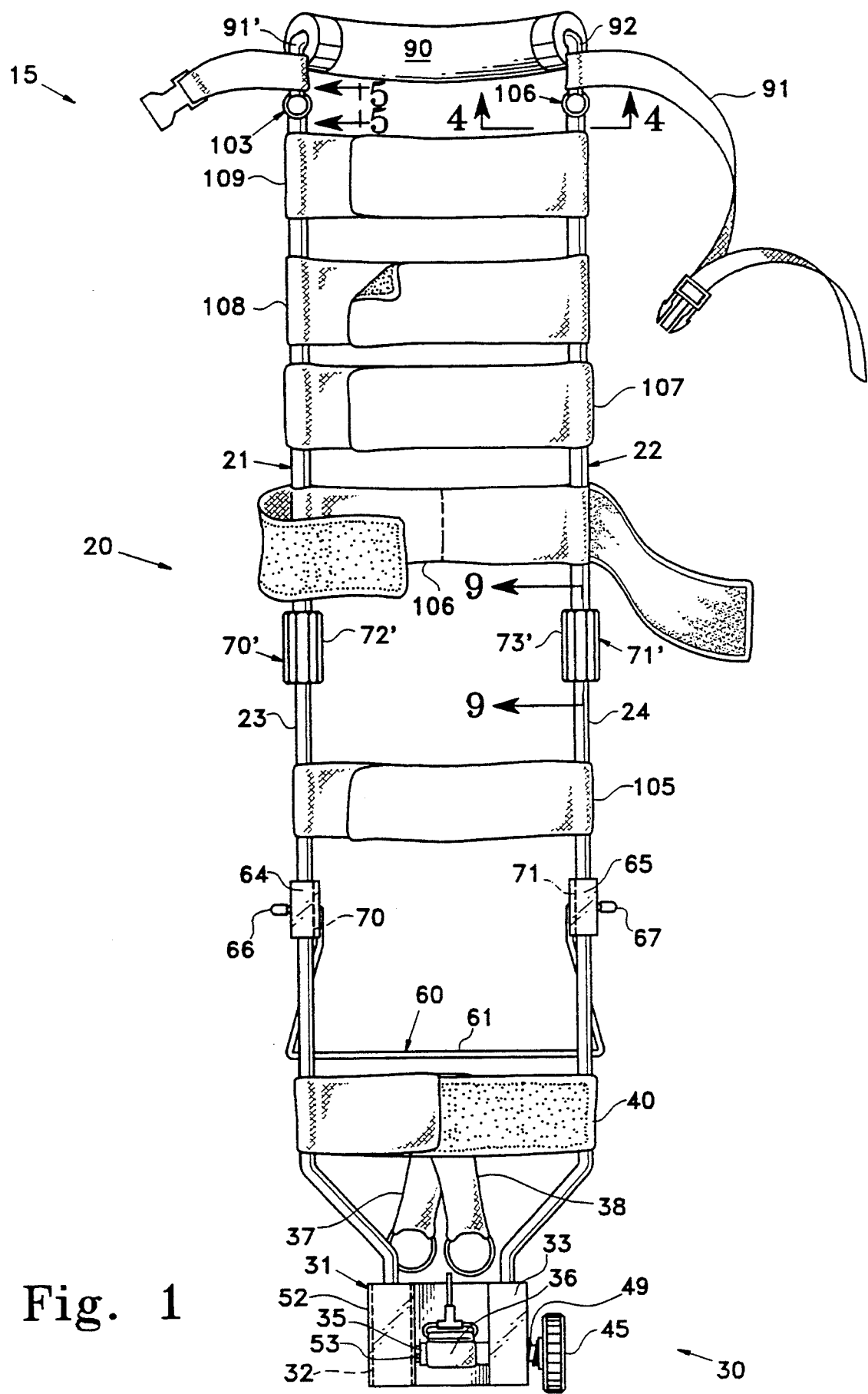
FIG. 1 is a plan view of a traction splint embodying the present invention.
Figure 2:
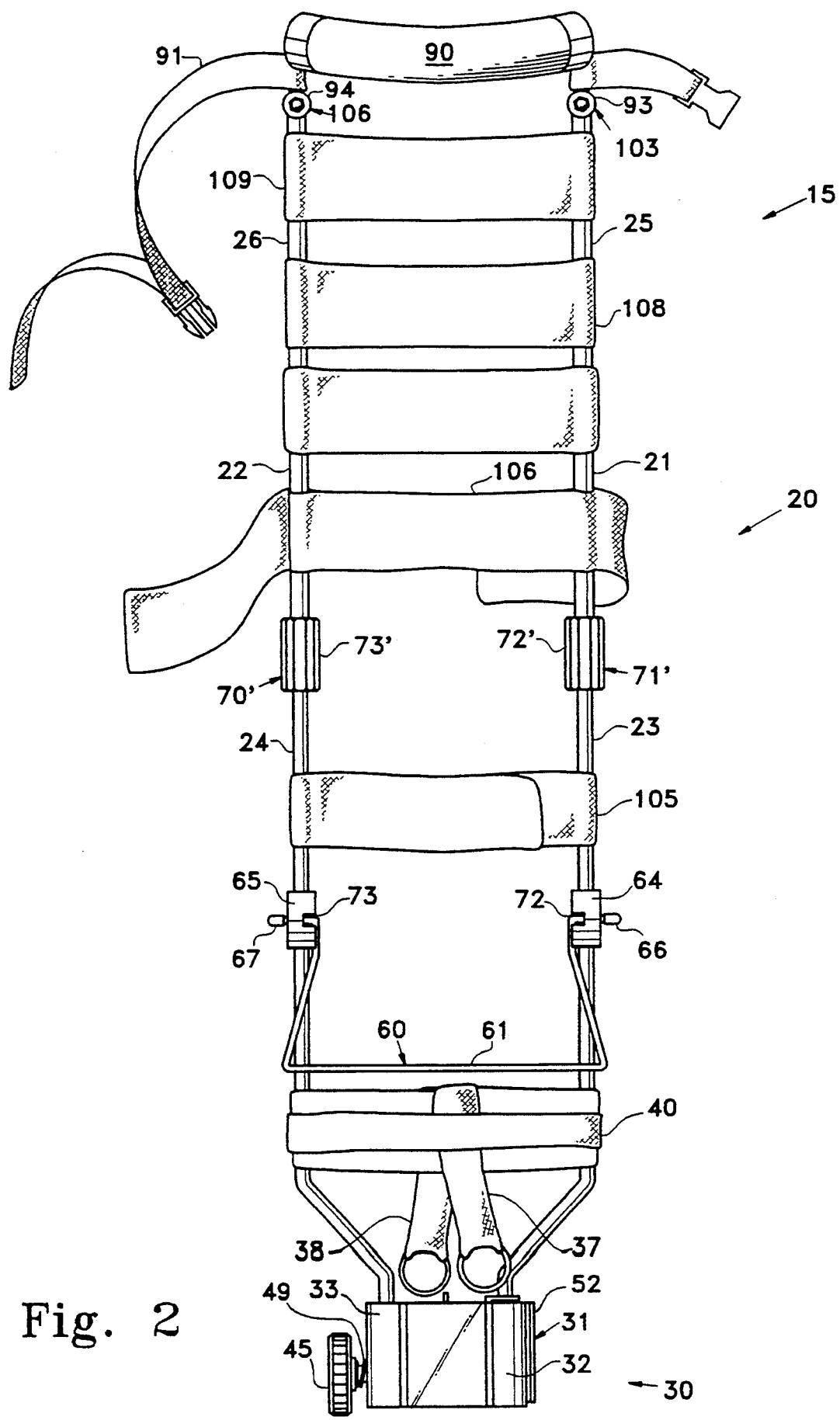
FIG. 2 is a bottom view of the traction splint shown in FIG. 1.
Figures 3, 4, 5:
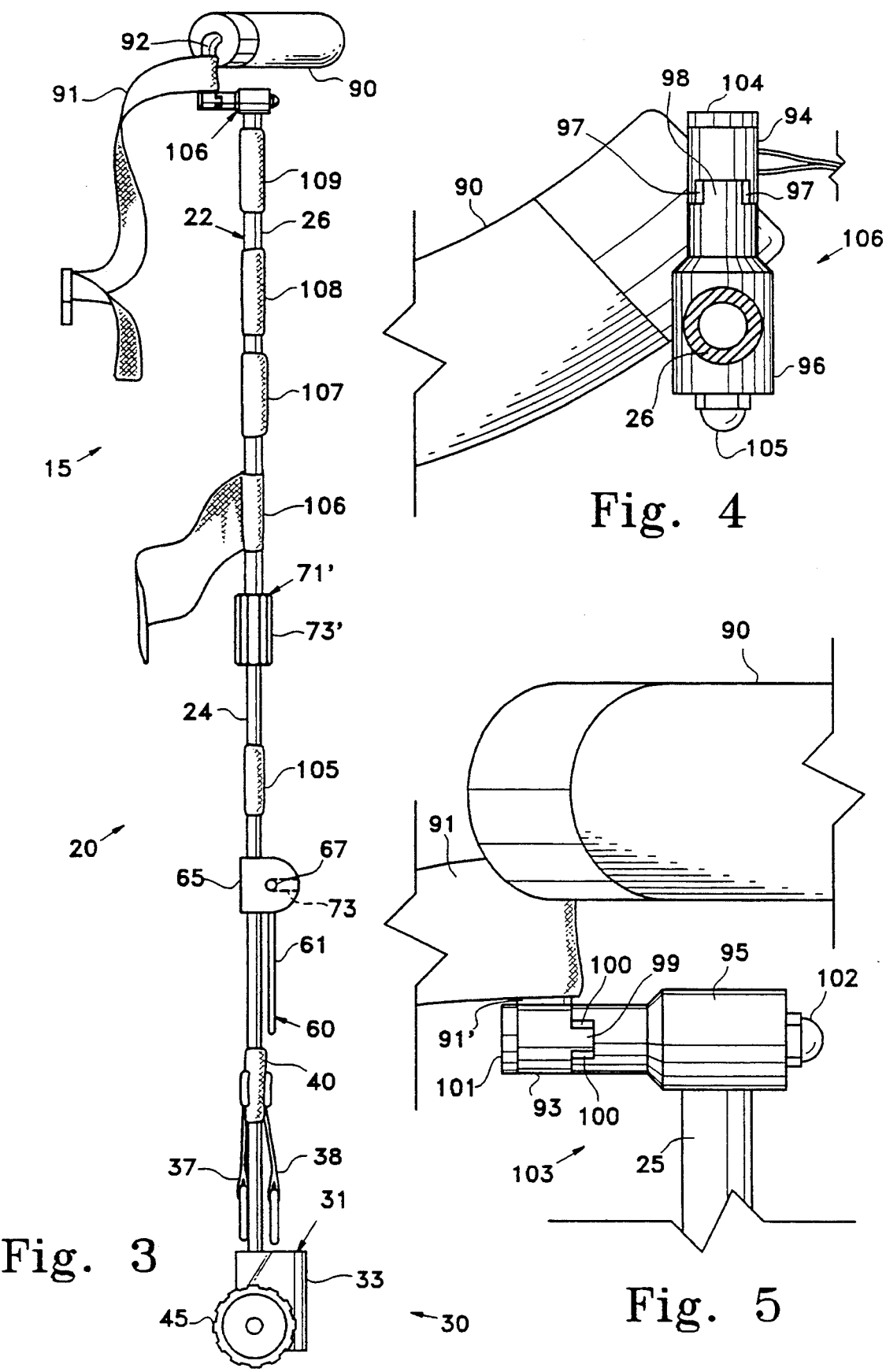
FIG. 3 is a side elevation view of the traction splint shown in FIGS. 1 and 2.
FIG. 4 is an enlarged fragmentary vertical sectional view taken along lines 4—4 of FIG. 1 and illustrating a pivotal connection between an ischial pad and a parallel side member of the frame of the traction splint shown in FIGS. 1-3.
FIG. 5 is an enlarged fragmentary elevation view of a pivotal connection between the ischial pad and a parallel side member of the frame of the traction splint taken along lines 5—5 of FIG. 1.

Illustrated in FIGS. 1-3 is a long bone traction splint 15 comprising a frame 20. The frame 20 includes parallel side members 21 and 22. The side members 21 and 22 include, respectively, parallel rods 23 and 24, and tubes 25 and 26, respectively. The rods 23 and 24 are received by the tubes 25 and 26, respectively. In the preferred embodiment, the rods 23 and 24 are made of steel and the tubes 25 and 26 are made of aluminum.

At the foot or forward end of the frame 20, the rods 23 and 24 are bent inwardly or at an angle toward one another and terminate in parallel segments. A suitable traction mechanism 30 (FIGS. 1-3 and 14) is supported at the foot of the frame 20 by the parallel segments of the rods 23 and 24 and, in the exemplary embodiment, is fixed thereto. The traction mechanism 30 is of the type used in the aforementioned REEL SPLINT 8800 Series traction splint.

The traction mechanism 30 includes a U-shaped base 31 with upstanding legs or ears 32 and 33, which receive the parallel segments of the rods 23 and 24 to be supported thereby. In the exemplary embodiment, the rods 23 and 24 are fixed to the legs 32 and 33, respectively. The legs or ears 32 and 33 also support a transverse shaft 35 (FIGS. 1 and 14) for rotation. Wrapped around the shaft 35 are layers of a belt 36 in the form of a roll. The free end of the belt 36 is detachably connected to straps 37 and 38 of a suitable ankle harness 40. The other end of the belt 36 is replaceably secured to the shaft 35. The ankle harness 40, in the exemplary embodiment, include suitable confronting pads secured to a strap made of a suitable cloth webbing. VELCRO fasteners releasably secure the free ends of the strap.

At one end of the traction mechanism 30 is a handle 45. Rotation of the handle 45 in one direction rotates the shaft 35 to apply traction tension to the ankle harness 40 through the straps 37 and 38. The shaft 35 is locked in the traction tension position by a ratchet dog 47 until released. Movement of the shaft 35 against the urgency of a spring 49 through the handle 45 and the rotation of the shaft 35 through the handle 45 in the opposite direction releases the free end of the belt 36 from traction tension. The free end of the belt 36 is also detachable from the straps 37 and 38.

At the end of the shaft 35 facing the dog 47 and the handle 45 is a ratched or toothed end 46 of the shaft 35 (FIG. 14) having an annular configuration. Between the handle 45 and the ratchet member 46 or the indent teeth of the shaft 35 is the ratchet dog or detent 47 having an annular configuration. A ratchet stud 48 is fixed at one end to the handle 45 and passes freely through the ratchet dog 47. The ratchet dog 47 is attached to the ear 33 through a pin 47′. At the other end thereof, the ratchet stud 48 enters and is pinned to the shaft 35 by a pin 54. The ratchet stud 48 is pinned to and is arranged to impart rotation to the shaft 35. The coil spring 49 surrounds the ratchet stud 48 and abuts against the enlarged diameter section of the ratchet handle 45 and against the ratchet dog or indent 47 in the recessed section of the indent 47 facing the handle 45.

During the tensioning operation of the traction mechanism 30, the handle 45 is rotated in one direction and imparts rotation to the shaft 35 through the ratchet stud 48 for applying tension to the ankle harness 40. Under the urgency of the spring 49, the detent 47 holds the shaft 35 in the tensioned state. To release the traction mechanism 30 from the tensioned state, the handle 45 is manually moved against the urgency of the spring 49 in the axial direction thereof toward the shaft 35 to move the shaft 35 in the axial direction thereof away from the detent 47. This action separates the shaft 35 from the detent 47, thus enabling the shaft 35 to be rotated for releasing the tension on the ankle harness 40. The shaft 35 is movable axially and is supported for rotation onto a shaft 51 that is fixed to the leg 32 of the U-shaped base 31. When the handle 45 is released, the coil spring 49 returns the handle 45 to its initial position for tensioning the shaft 35 and the ankle harness 40 and returns the shaft 35 to its initial position for releasably holding the shaft 35 in its rotated adjusted tensioned state by the detent of the ratchet dog 47. A locking member 52 is formed with a stop 53 thereon. When the locking member 52 is in a locked position, the stop 53 prevents the shaft 35 from moving axially by the movement of the handle 45 against the urgency of the spring 49 and thereby prevents the traction mechanism 30 from inadvertently releasing the tension on the ankle harness 40. When the locking member 52 is in the unlocked position, the shaft 35 is axially movable by the movement of the handle 45 against the urgency of the spring 49 to release the shaft 35 from the ratchet dog 47 and to release the tension on the harness 40. When the locking member 52 is in the locked position, the stop 53 is in the path of axial movement of the shaft 35 to prevent the axial movement of the handle 45 against the urgency of the spring 49 and, thus, preventing the subsequent release of the shaft 35 from the detent of the ratchet dog 47 and the axial movement of the shaft 52 toward the leg 32. When the locking member 52 is in the unlocked position, the stop 53 is removed from the path of axial movement of the shaft 35 enabling the axial movement of the shaft 35 toward the leg 32. A suitable pin 54 retains the ratchet stud 48 secured to the shaft 35. A spring loaded stop 53 and a spring 53′ maintains the locking member 52 in the selected position either in a locking state or in an unlocking state. The stop 53 is displaced against the urgency of the spring 53′ by a manual force applied to the locking member 52. The release of the manual force enables the locking member 52 to be maintained in its selected position.

The shaft 35 is locked in place by the ratchet dog 47. Movement of the handle 45 against the urgency of the spring 49 releases the shaft 35 from the ratchet dog 47, enabling one hand traction increase and reduction. After the traction adjustment is made, the locking member 52 is engaged to disable operation of the traction mechanism 30 for preventing occasional traction loss. The locking member 52 enables one hand control over ratchet locking and ratchet releasing.

A suitable retractable stand 60 (FIGS. 1–3 and 13) is located in the vicinity of the foot of the traction splint 15 and, in the exemplary embodiment, is disposed rearwardly of the ankle harness 40. The stand 60 comprises a U-shaped support 61. In the exemplary embodiment, the U-shaped support 61 is of a relatively narrow steel rod. The free ends of the legs of the support 60 are directed outwardly and are received, respectively, by suitable bores formed in retaining brackets 64 and 65, respectively. In the exemplary embodiment, the brackets 64 and 65 are made of aluminum. The free ends of the legs of the U-shaped support 61 project outwardly of the brackets 64 and 65, respectively. Suitable caps, in the exemplary embodiment, are supported by the free ends of the legs of the U-shaped support 61 to form suitable plungers 66 and 67. On the inwardly confronting walls of the brackets 64 and 65 are formed horizontal grooves 70 and 71 and vertical grooves 72 and 73. In the exemplary embodiment, the caps are made of rubber or a hardened flat plastic.

When the stand 60 is in an erect position to lift or raise the frame 20, the legs of the U-shaped support 61 occupy the vertical grooves 72 and 73, respectively, and the stand 60 is releasably retained in the erect position. To retract the stand 60 to lower the frame 20, the plungers 66 and 67 are actuated manually toward one another to temporarily flex the legs of the U-shaped support 61 out of the vertical groove 72 and 73. Thereupon, the U-shaped support 61 is pivoted toward the frame 20 until the legs thereof are received by and releasably retained in the horizontal grooves 70 and 71. To lift the frame 20, the plungers 66 and 67 are actuated as above-described and the legs of the U-shaped support 61 are removed from the horizontal grooves 70 and 71. Thereupon, the U-shaped support 61 is pivoted to the erect position until the legs of the U-shaped support 61 are received by and releasably retained in the vertical grooves 72 and 73.

The U-shaped support 61, in the exemplary embodiment, is made of steel and is sufficiently temporarily yieldable upon the actuation of the plungers 66 and 67 to resiliently flex in the manner aforementioned.

As previously described, the rods 23 and 24 are telescopically received by the tubes 25 and 26, respectively. By retracting and extending the rods 23 and 24 into and out of the tubes 25 and 26, respectively, the extent of the respective rods is adjusted. For securing the tubes 25 and 26, respectively, in selected positions relative to the rods 23 and 24, suitable releasable locking devices 70' and 71' (FIGS. 1–3, 9 and 10) are provided. The locking devices 70' and 71' are similar in construction and in operation. The locking devices 70' and 71' include cylindrically-shaped nuts 72' and 73', respectively. The nuts 72' and 73' are formed with axial bores 74 and 75, respectively. The inner walls of the nuts 72' and 73' surrounding the bores 74 and 75, respectively, are threaded. The ends of tubes 25 and 26 facing the rods 23 and 24, respectively, are formed with external threads and are received by the bores 74 and 75, respectively, of the nuts 72' and 73', respectively.

Disposed within the bores 74 and 75 of the nuts 72' and 73', respectively, are temporarily yieldable collets 80 and 81. The collets 80 and 81, in the exemplary embodiment, are made of brass. At the ends of the rods 23 and 24 facing rearwardly of the frame 20 are internally threaded collet stops 82 and 83, respectively, with bearing surface ends to prevent the collets 80 and 81 from being removed from the rods 23 and 24, respectively. The rods 23 and 24 pass freely through the nuts 72' and 73', respectively, and the collets 80 and 81, respectively, and enter the tubes 25 and 26, respectively. The rods 23 and 24 are detachably secured to the stops 82 and 83, respectively, through threaded engagement. By rotating the nuts 72' and 73' into threaded engagement with the tubes 25 and 26, respectively, to move the nuts 72' and 73' toward the rearward direction of the frame 20, the collets 80 and 81 are urged, respectively, toward the abutting ends of the tubes 25 and 26, respectively, and are temporarily compressed by the walls surrounding the bores 74 and 75, respectively, until a tight releasable locking engagement is made between the rods 23 and 24, and the tubes 25 and 26, respectively. The compression of the collets 80 and 81 causes the collets 80 and 81 to releasably grip the rods 23 and 24, respectively. The releasable locking devices 70 and 71 are of the type used on the aforementioned REEL SPLINT 8800 Series traction splint.

At the rearward end of the frame 20 is a suitable ischial pad 90 (FIGS. 1–3). Ischial pads are well-known in the art and are made of suitable foam material surrounding a bar. Adjacent the ischial pad 90 is a suitable ischial strap 91. The ischial pad 90 has a concave cradle configuration as viewed in FIG. 1. In the preferred embodiment, the ischial pad 90 has a configuration of generally a half of a ring or half of a toroid. The ischial strap 91 is made of suitable cloth webbing in which the free ends, in the exemplary embodiment, are held together by a snap release fastener.

At the opposite ends of the ischial pad 90 are fixedly attached inwardly turned support rods 91' and 92. The free ends of the support rods 91' and 92 are affixed to tubular pivotal members 93 and 94, respectively (FIGS. 3–6, 11 and 12). The axes of the tubular pivotal members 93 and 94 are disposed perpendicular to the axes of the tubes 25 and 26, respectively (FIGS. 3–6). Fixed to the rearward ends of the tubes 25 and 26, respectively, are tubular members 95 and 96. The axes of the tubular members 95 and 96 are at right angles to the axes of the tubes 25 and 26, respectively, and are coextensive with the axes of the tubular pivotal members 93 and 94, respectively.

Figure 6:
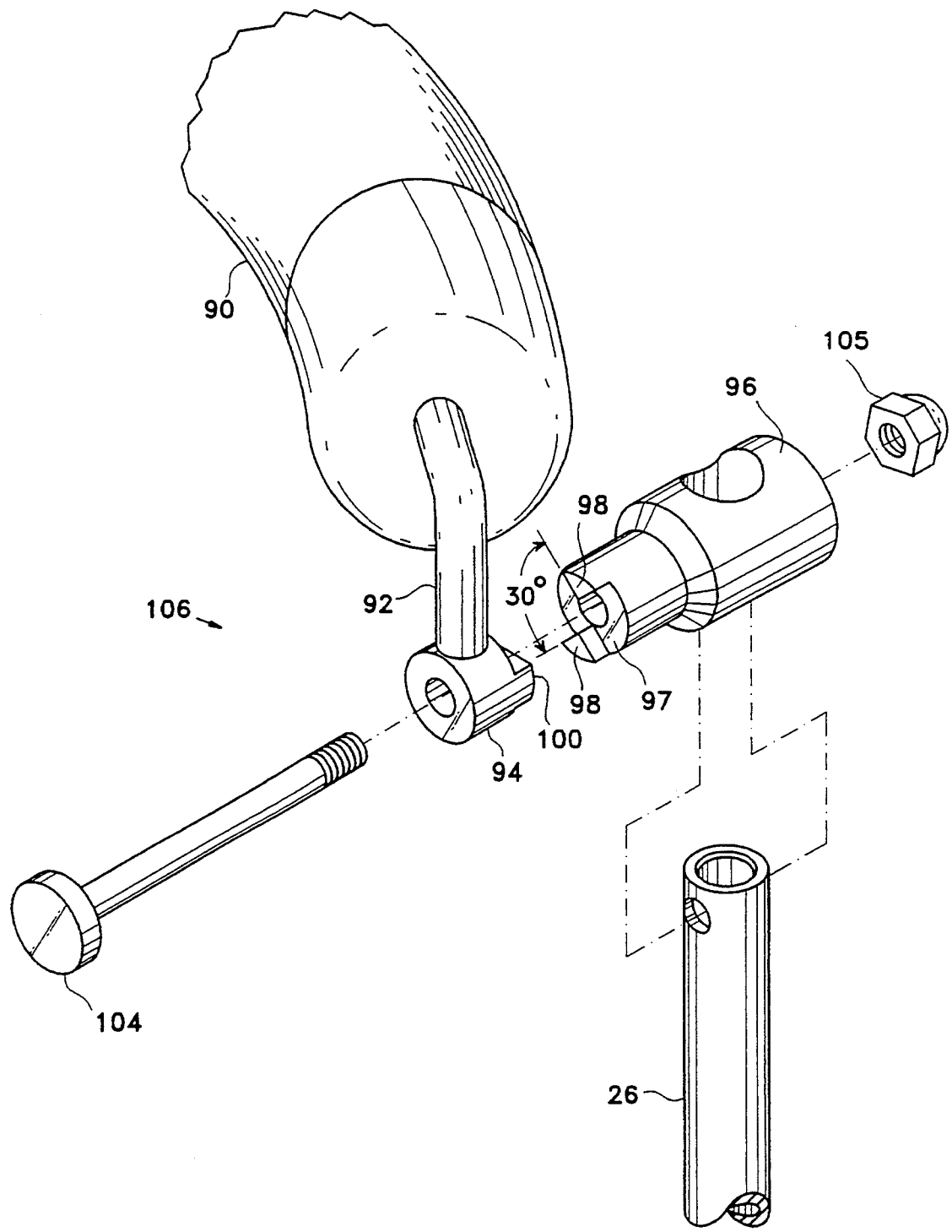
FIG. 6 is an enlarged, exploded fragmentary view of the pivotal connection between the ischial pad and the parallel side member shown in FIG. 4.

The tubular pivotal members 93 and 94 are disposed above and adjacent to the tubular members 95 and 96, respectively (FIGS. 3 and 4). The upper walls of each of the tubular members 95 and 96 along the perimetric ends thereof are formed with successive or alternate grooves 97 and ridges 98 (FIGS. 4 and 6). The lower walls of each of the tubular pivotal members 93 and 94 along the perimetric ends thereof are formed with ridges 99 and grooves 100. The grooves and ridges of the tubular members 95 and 96 and the tubular pivotal members 93 and 94 have a generally annular square wave configuration with the ridges of the tubular pivotal members 93 and 94 disposed successively within the grooves of the tubular members 95 and 96, and with the ridges of tubular members 95 and 96 disposed successively within the grooves of the tubular pivotal members 93 and 94 (FIGS. 4-6). A threaded rod 101 passes freely through the tubular pivotal member 93 and is threaded into and through the tubular member 95. A head on the rod 101 seats on top of the tubular pivotal member 93 and a nut 102 is received in threaded engagement with the tubular member 95 and the portion of the rod 101 below the tubular member 95 to retain the pivot arrangement 103 as a pivot assembly. The tubular pivotal member 93 is pivotal relative to the tubular member 95.

In a similar manner, a threaded rod 104 passes freely through the tubular pivotal member 94 and the tubular member 96. A head on the rod 104 rests on the top of the tubular pivotal member 94 and a nut 105 is received in threaded engagement with the threaded tubular member 96 and with the portion of the threaded rod 104 below the tubular member 96 to retain the pivot arrangement 106 as a pivot assembly. The tubular pivotal member 94 is pivotal relative to the tubular member 96.

The pivotal arrangement 106 is similar in structure and operation to the pivotal arrangement 103. The components of the pivotal arrangements 103 and 106, in the exemplary embodiment, are made of steel or aluminum.

The ridges and grooves of the tubular pivotal members 93 and 94 and the ridges and grooves of the tubular members 95 and 96 are constructed and arranged, when placed in confronting and contiguous relation, to limit or restrict the rotation of each of the tubular pivotal members 93 and 94, respectively, relative to the tubular members 95 and 96, respectively. In the exemplary embodiment, the angular rotation of each of the tubular pivotal members 93 and 94 relative to the tubular members 95 and 96, respectively, is limited or restricted up to 35°. In the preferred embodiment, the angular rotation of each of the tubular pivotal members 93 and 94 relative to the tubular members 95 and 96, respectively, is limited or restricted up to 30° (FIGS. 11 and 12). In this manner, the pivotal movement of the ischial pad 90, in the exemplary embodiment, is limited or restricted up to 35° relative to the frame 20. In the preferred embodiment, the pivotal movement of the ischial pad 90 is limited or restricted up to 30° relative to the frame 20.

Disposed along the frame in a generally transverse direction across the frame 20 are suitable straps 105-109 for releasably securing the patient to the frame 20 (FIGS. 1-3). The straps 105-109 are made of suitable cloth webbing and the free ends thereof are releasably secured together by VELCRO fasteners.

Although the ischial pad 90 extends generally transversely relative to the frame 20, the ischial pad 90 is selectively pivotal relative to the frame 20 in the manner above-described. In the exemplary embodiment, the selective pivotal movement of the ischial pad 90 is limited or restricted up to 35° relative to the frame 20. In the preferred embodiment, the selective pivotal movement of the ischial pad 90 is limited or restricted up to 30° relative to the frame 20.

Figure 7:
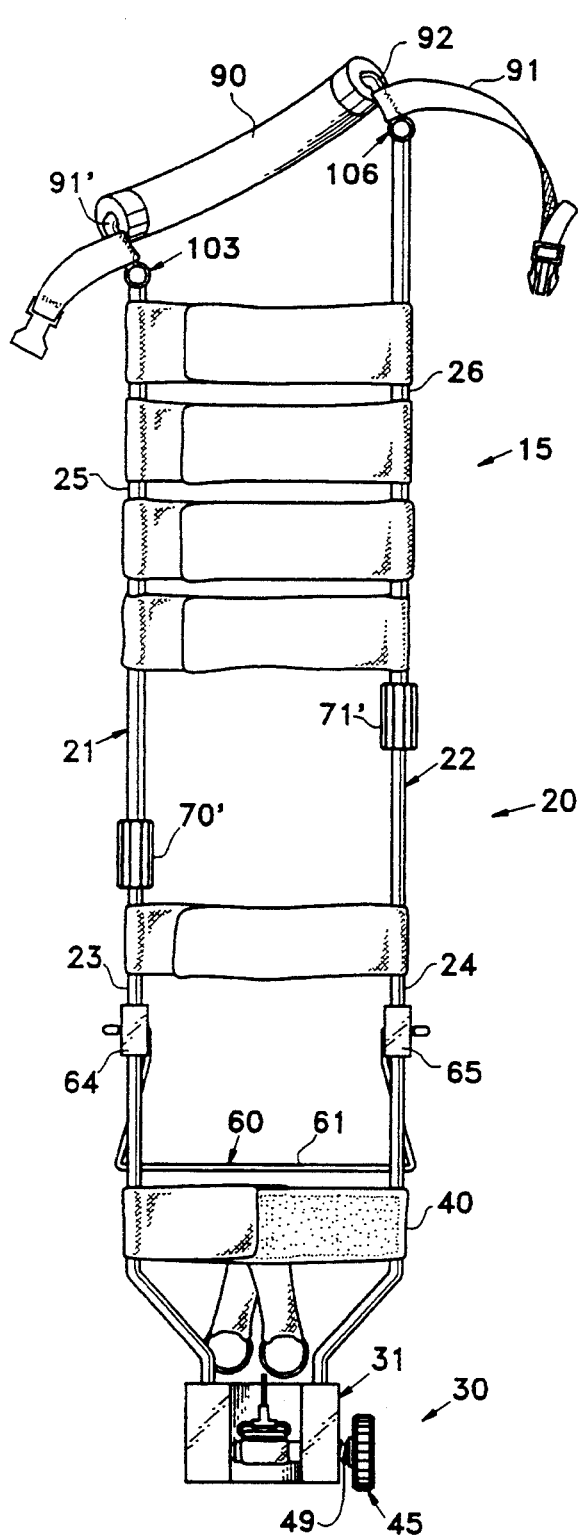
FIG. 7 is a diagrammatic plan view of the long bone traction splint shown in FIGS. 1-3 illustrating the ischial pad pivoted in one direction.
Figure 8:
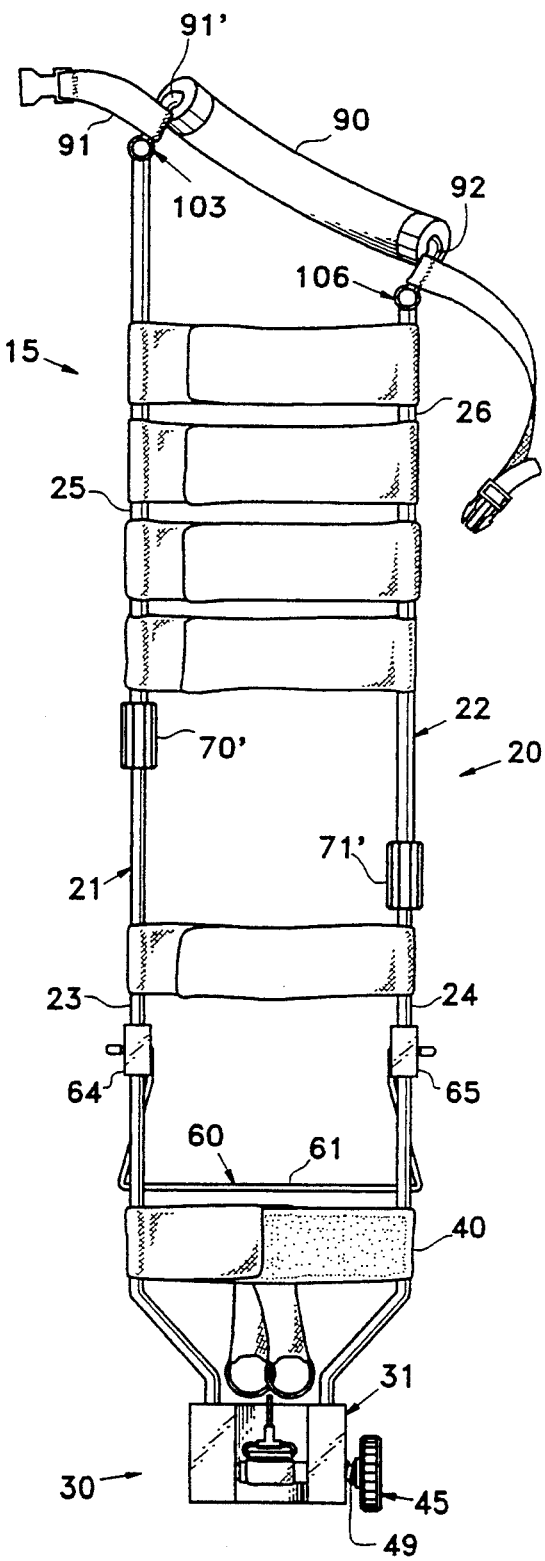
FIG. 8 is a diagrammatic plan view of the long bone traction splint shown in FIGS. 1-3 illustrating the ischial pad pivoted in an opposite direction.
Figure 14:
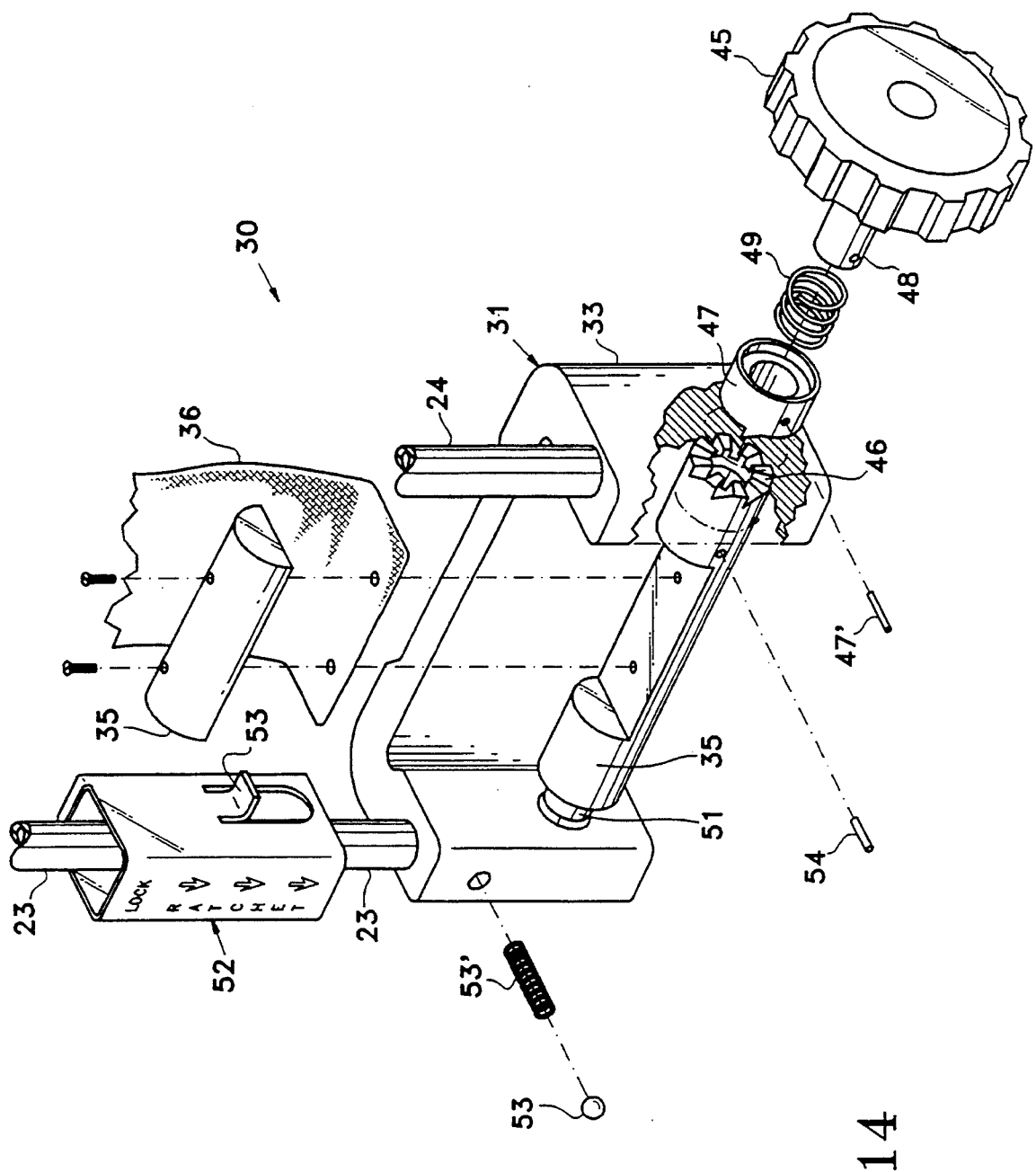
FIG. 14 is a fragmentary, enlarged, exploded perspective view of the traction mechanism for the traction splint shown in FIGS. 1-3.

In the preferred embodiment, the adjustment of the extent of the rods 23 and 24, respectively, and the adjustment of the selective angular position of the ischial pad 90 relative to the frame 20 are carried out simultaneously. While one or more of the releasable locking devices 70' and 71' is in an unlocked state, the adjustment of the extent of one or more of the rods 23 and 24 is made by relative telescopic displacement between the released one or more of the rods 23 and 24 and the tubes 25 and 26, respectively (FIGS. 7 and 8). Simultaneously therewith the ischial pad 90 is angularly displaced relative to the frame 20 in accordance with the longitudinal distance between the releasable locking devices 70 and 71. The pivotal movement of the ischial pad 90 relative to the frame 20 is limited in the manner heretofore described. It is apparent that the length of the frame 20 can be adjusted while both releasable locking devices 70' and 71' are in the unlocked state and then the locking devices 70' and 71' are rotated to lock the frame 20 in the adjusted length. By unlocking one of the releasable locking devices 70' and 71', the length of the associated side member 21 and 22 can be adjusted, and also the angle of the ischial pad 90 can be adjusted simultaneously and limited to a selected angular orientation up to 35° relative to opposite side adjustment. The rotating of the free locking device and the adjusted length of the associated side member locks the associated side member at the adjusted length and locks the ischial pad 20 at the adjusted angle up to a maximum of 35° relative to the tubular members 95 and 96.

What is claimed is:

1. A traction splint comprising:
A. a frame having parallel side members, each of said side members comprising:
   (a) a tube,
   (b) a rod telescopically received by said tube for adjusting the extent of said rod, and
   (c) a releasable locking device receiving said rod and said tube for releasably retaining the adjusted extent of said rod;
B. an ischial pad disposed generally transversely of said side members, said ischial pad having oppositely directed ends; and
C. pivotal means interconnecting each end of said ischial pad, said pivotal means interconnecting said ends of said ischial pad to said side members, respectively, for angularly positioning said ischial pad relative to said frame, said pivotal mean selectively limiting the angular positioning of said ischial pad relative to said frame,
D. each of said tubes having one end adjacent said ischial pad, said pivotal means joining the ends of said ischial pad to adjacent ends of said tubes, respectively, for adjusting simultaneously the extent of one or more of said rods and the angle of said ischial pad relative to said frame while at least one of said releasable locking devices enables the extent of one or more of said rods to be adjusted, each of said tubes having an axis and each of said pivotal means comprising:
   (a) a tubular pivotal member attached to one end of said ischial pad, said tubular pivotal member having an axis disposed at right angles to the axis of the tube adjacent said one end of said ischial pad, and
   (b) a tubular member fixed to one end of said tube adjacent said one end of said tubular pivotal member, said tubular member having an axis coextensive with the axis of said tubular pivotal member, said tubular pivotal member and said adjacent tubular member having perimetric confronting ends,
   (c) said tubular pivotal member and said adjacent tubular member at the perimetric confronting ends thereof being formed with interposed ridges and grooves for selectively limiting the angular positioning of the ischial pad relative to said frame.

2. A traction splint as claimed in claim 1 wherein each of said releasable locking devices comprises:
(a) a cylindrical nut with an axial bore for receiving one of said tubes and the rod received by said one tube, said axial bore for said cylindrical nut being surrounded by an internal threaded wall;
(b) said tube being formed with external threads for threaded engagement with the internal threaded wall of said nut; and
(c) a yieldable collet disposed within the bore of said nut, said collet being arranged to grip said rod telescopically received by said one tube, said collet being temporarily compressible for releasably gripping said rod telescopically received by said one tube as said nut is threaded on said one tube for releasably locking said rod telescopically received by said one tube with said one tube for retaining the adjusted extent of said rod telescopically received by said one tube.

3. A traction splint comprising:
A. a frame having parallel side members, each of said side members comprising:
(a) a tube,
(b) a rod telescopically received by said tube for adjusting the extent of said rod, and
(c) a releasable locking device receiving said rod and said tube for releasably retaining the adjusted extent of said rod;
B. an ischial pad disposed generally transversely of said side members, said ischial pad having oppositely directed ends; and
C. pivotal means interconnecting each end of said ischial pad, said pivotal means interconnecting said ends of said ischial pad to said side members, respectively, for angularly positioning said ischial pad relative to said frame, said pivotal mean selectively limiting the angular positioning of said ischial pad relative to said frame, said pivotal means selectively limiting the angular position of said ischial pad relative to said frame to an angle not exceeding 35°,
D. each of said tubes having one end adjacent said ischial pad, said pivotal means joining the ends of said ischial pad to adjacent ends of said tubes, respectively, for adjusting simultaneously the extent of one or more of said rods and the angle of said ischial pad relative to said frame while at least one of said releasable locking devices enables the extent of one or more of said rods to be adjusted, each of said tubes having an axis and each of said pivotal means comprising:
(a) a tubular pivotal member attached to one end of said ischial pad, said tubular pivotal member having an axis disposed at right angles to the axis of the tube adjacent said one end of said ischial pad, and
(b) a tubular member fixed to one end of said tube adjacent said one end of said tubular pivotal member, said tubular member having an axis coextensive with the axis of said tubular pivotal member, said tubular pivotal member and said adjacent tubular member having perimetric confronting ends,
(c) said tubular pivotal member and said adjacent tubular member at the perimetric confronting ends thereof being formed with interposed ridges and grooves for selectively limiting the angular displacement of said ischial pad relative to said frame up to 35°.

4. A traction splint as claimed in claim 3 wherein each of said releasable locking devices comprises:
(a) a cylindrical nut with an axial bore for receiving one of said tubes and the rod received by said one tube, said axial bore for said cylindrical nut being surrounded by an internal threaded wall;
(b) said tube being formed with external threads for threaded engagement with the internal threaded wall of said nut; and
(c) a yieldable collet disposed within the bore of said nut, said collet being arranged to grip said rod telescopically received by said one tube, said collet being temporarily compressible for releasably gripping said rod telescopically received by said one tube as said nut is threaded on said one tube for releasably locking said rod telescopically received by said one tube with said one tube for retaining the adjusted extent of said rod telescopically received by said one tube.

5. A traction splint comprising:
A. a frame having parallel side members, each of said side members having a tube;
B. an ischial pad disposed generally transversely of said side members, said ischial pad having oppositely directed ends; and
C. pivotal means interconnecting each end of said ischial pad, said pivotal means interconnecting said ends of said ischial pad to said side members, respectively, for angularly positioning said ischial pad relative to said frame, said pivotal mean selectively limiting the angular positioning of said ischial pad relative to said frame, each of said tubes having an axis, each of said pivotal means comprising:
(a) a tubular pivotal member attached to one end of said ischial pad, said tubular pivotal member having an axis disposed at right angles to the axis of the tube adjacent said one end of said ischial pad; and
(b) a tubular member fixed to one end of said tube adjacent said one end of said tubular pivotal member, said tubular member having an axis coextensive with the axis of said tubular pivotal member, said tubular pivotal member and said adjacent tubular member having perimetric confronting ends,
(c) said tubular pivotal member and said adjacent tubular member at the perimetric confronting ends thereof being formed with interposed ridges and grooves for selectively limiting the angular positioning of the ischial pad relative to said frame.

* * * * *